United States Patent [19]

Martin et al.

[11] Patent Number: 5,807,585
[45] Date of Patent: *Sep. 15, 1998

[54] METHOD OF PRESERVING OPHTHALMIC SOLUTION AND COMPOSITIONS THEREFOR

[75] Inventors: Stephen M. Martin, Roswell; Fu-Pao Tsao, Lawrenceville, both of Ga.

[73] Assignee: Ciba Vision Corporation, Duluth, Ga.

[ * ] Notice: The term of this patent shall not extend beyond the expiration date of Pat. No. 5,576,028.

[21] Appl. No.: 761,174

[22] Filed: Dec. 6, 1996

Related U.S. Application Data

[63] Continuation of Ser. No. 709,452, Sep. 5, 1996, Pat. No. 5,725,887, which is a continuation of Ser. No. 259,201, Jun. 13, 1994, abandoned, which is a division of Ser. No. 99,986, Jul. 29, 1993, abandoned, which is a continuation of Ser. No. 968,224, Oct. 29, 1992, abandoned, which is a continuation of Ser. No. 733,485, Jul. 22, 1991, abandoned, which is a continuation of Ser. No. 376,083, Jul. 6, 1989, abandoned, which is a continuation-in-part of Ser. No. 229,163, Aug. 4, 1988, abandoned.

[51] Int. Cl.$^6$ ................................................ A61K 31/16
[52] U.S. Cl. ........................................ 424/613; 514/912
[58] Field of Search ............................. 514/912; 424/613

[56] References Cited

U.S. PATENT DOCUMENTS 4,889,689  12/1989  Tsao .......................................... 422/30

*Primary Examiner*—Zohreh Fay
*Attorney, Agent, or Firm*—Michael U. Lee; R. Scott Meece

[57] ABSTRACT

A preservative for ophthalmic solutions having an active ingredient is provided, having a hydrogen peroxide content of about 0.001% to about 0.10% by weight; and diethylene triamine penta(methylene phosphonic acid) or a physiologically compatible salt thereof, present at about 0.002% to 0.03% by weight and/or 0.005% to about 0.20% by weight of 1-hydroxyethylidene-1,1-diphosphonic acid, or physiologically acceptable salt thereof.

16 Claims, No Drawings

METHOD OF PRESERVING OPHTHALMIC SOLUTION AND COMPOSITIONS THEREFOR

This application is a continuation of application Ser. No. 08/709,452, filed on Sep. 5, 1996, now U.S. Pat. No. 5,725,887, which is a continuation of application Ser. No. 259,204, filed on Jun. 13, 1994, abandoned, which is a division of application Ser. No. 99,986, Jul. 29, 1993, abandoned, which is a continuation of application Ser. No. 968,224, Oct. 29, 1992, abandoned, which is a continuation of application Ser. No. 733,485, filed on Jul. 22, 1991, abandoned, which is a continuation of application Ser. No. 376,083, filed on Jul. 6, 1989, abandoned, which is a continuation-in-part of application Ser. No. 229,163, filed on Aug. 4, 1988, abandoned.

The present invention relates to a method of preserving ophthalmic solutions with trace amounts of stabilized peroxy compounds. More particularly, this invention relates to the use of stabilized trace amounts of hydrogen peroxide as preservative in buffered saline for eye care solutions.

Hydrogen peroxide is a well-known germicidal agent. For example, hydrogen peroxide in the form of a relatively dilute solution, e.g. about 0.5 to 6% by weight in water, is known to be effective as a disinfectant for use with contact lenses in order to kill any contaminating microorganisms.

One drawback with unstablized dilute hydrogen peroxide solutions, however, is that without the use of a stabilizer or a combination of stabilizers, the aqueous peroxide solutions characteristically decompose over a period of time. The rate at which such dilute hydrogen peroxide solutions decompose will, of course, be dependent upon such factors as pH and the presence of trace amounts of various metal impurities, such as copper or chromium, which may act to catalytically decompose the same. Moreover, at moderately elevated temperatures, the rate of decomposition of such dilute aqueous hydrogen peroxide solutions is greatly accelerated.

A large variety of stabilizers have been proposed for use with hydrogen peroxide to deactivate trace catalytic impurities, including stannous salts, ethylene diamine tetra acetic acid, and the like. For example, U.S. Pat. No. 3,860,391 discloses bleaching compositions containing hydrogen peroxide and, as a stabilizer, amino lower alkylene phosphates, including diethylene triamine penta(methylene phosphonic acid) or salts thereof, and/or hydroxy alkane phosphates, with or without additional stabilizer constituents, and adjusted to a pH of between about 9.0 and 12.0 with, e.g. sodium hydroxide, for the bleaching of cellulosic materials. Exemplified are compositions having a pH of 12.0. However, such highly basic compositions are undesirable in ophthalmically-related solutions, including eyewashes and contact lens cleaning solutions.

Also, British Patent No. 1,500,707 discloses a contact lens sterilizing solution using hydrogen peroxide with 200–2000 ppm of a phosphate [pyrophosphate] stabilizer at a pH of 4.5.

However, the disinfection is not carried out at a pH consistent with the ocular environment since the pH needs to be elevated to around 7. Also, the peroxide must be eliminated so as to make the solution compatible with the eye.

U.S. Pat. No. 4,304,762 discloses stabilization of aqueous hydrogen peroxide by addition of diethylenetriamine penta(methylene phosphonic acid) or a salt thereof at a pH of about 7. However, the stabilizing phosphonate compound is reported to be particularly effective for use with alkaline hydrogen peroxide solutions. Further these solutions are disclosed as being of use as a base for liquid bleach products. There is neither any hint that trace amounts of hydrogen peroxide are effectively stabilized nor is there any indication that hydrogen peroxide might be used as a preservative for an ophthalmic solution.

Some of the eye care solutions commercially available today use benzalkonium chloride, rather than hydrogen peroxide, as a preservative. For example, contact lens solutions typically contain 0.9% sodium chloride, buffers, surfactants, wetting agents, and 0.002 to 0.01% benzalkonium chloride. Benzalkonium chloride is also used in other products, including isotonic decongestant ophthalmic solutions, such as Visine® eyedrops manufactured by the Leeming Division of Pfizer, Inc.

A problem exists, however, in that benzalkonium chloride, being cationic in character, reacts with proteins found in the ocular environment and causes unwanted deposits on soft contact lenses. Benzalkonium chloride and its analogs are also taken up by lens material and can have a deleterious effect on the structure of the lens [Davis, S. S. et al., "The Adsorption of Cationic Antimicrobial Agent Onto PolyHema", Colloids and Surfaces, 12, 203–212 (1984)]. In addition, benzalkonium chloride is inactivated by many compounds, including those associated with cotton and nylon fibers. Furthermore, in Swan, K. C., "Reactivity of the Ocular Tissues to Wetting Agents", Am. J. Ophthalmol., 27, 118 (1944), it was noted that repeated use of benzalkonium chloride at concentrations of 1:5000 or stronger can denature the corneal protein and cause irreversible damage. It was also found that 0.04% to 0.05% solutions of benzalkonium chloride can cause superficial puncture disturbance of the corneal epithelium.

Other preservatives currently in use include thimerosal, which can cause a sensitivity reaction to the eye, and sorbic acid, which commonly causes lens discoloration. The disadvantages of the commonly used preservatives such as thimerosal, benzalkonium chloride and others are discussed in the following literature: M. Sibley, et al., "Understanding Sorbic Acid-Preserved Contact Lens Solutions", International Contact Lens Clinic, 11 (9), 531 (1984); M. Orron, et al., "Measurement of Preservative Binding with Soflens® (polymacon) Contact Lens", Aust. J. Optom., 59, 277 (1976); and M. Akers, "Considerations in selecting antimicrobial preservative agents for parenteral product development", Pharmaceutical Technology, May, p. 36 (1984).

OBJECTS OF THE INVENTION

An object of the invention is to provide a preservative for all manner of ophthalmic and ophthalmically related solutions having hydrogen peroxide compatible components which does not suffer from the aforementioned defects.

Another object of the invention is to provide preserved ophthalmic and ophthalmically related solution formulations which are free of the known art preservatives.

Yet another object of the invention is to provide a means of preserving ophthalmic and ophthalmically related solutions with hydrogen peroxide or hydrogen peroxide generating components.

SUMMARY OF THE INVENTION

Surprisingly, the disadvantages of the prior art preservatives are overcome by stabilized trace peroxy compounds provided by the present invention which may be used as a preservative in ophthalmic solutions such as eye lubrication solutions, ophthalmic drug formulations and contact lens solutions.

The low levels of peroxy compounds are below the commercially suitable amounts necessary for the peroxy compound to act as a disinfectant and is either low enough to be tolerable to direct application to the eye or may be made so by simple dilution with water or saline. In addition, the pH is also compatible with the ocular environment or upon the dilution indicated above is made so. For ophthalmic solutions (those which are to be instilled in the eye directly), the peroxy content and pH must per se be in the "ocular compatible range". Ophthalmic related solutions (those which are used in conjunction with contact lenses, other than "comfort or lubricating" drops which may be for instillation directly to the eye) may have appreciably higher peroxy content, but are intended to be diluted before being instilled in the eye or are used in such small amounts in the eye, that natural tear fluid dilution is sufficient to convert that solution to a solution which is compatible with the ocular environment.

The invention therefore relates to hydrogen peroxide or a source of hydrogen peroxide in trace amounts as a preservative for an ophthalmic solution, said hydrogen peroxide being especially effectively stabilized by addition of diethylene triamine penta(methylene phosphonic acid) or 1-hydroxyethylidene-1,1-diphosphonate, to the use of said stabilized trace amounts of hydrogen peroxide for preserving an ophthalmic solution, to ophthalmic solutions so preserved, to the manufacture of so preserved ophthalmic solutions and to a method of preserving any ophthalmic solution by adding thereto said stabilized trace amounts of stabilized hydrogen peroxide or a source of hydrogen peroxide.

For example, the trace amount of the hydrogen peroxide in these ophthalmic solutions ranges from about 0.001% (10 ppm) to about 0.10% (1000 ppm) by weight and is stabilized by about 0.002% (20 ppm) to about 0.03% (300 ppm) by weight of diethylene triamine penta(methylene phosphonic acid) or a physiologically compatible salt thereof.

Alternatively or additionally from 0.005% to about 0.2% by weight of 1-hydroxyethylidene-1,1-diphosphonic acid and/or from about 0.005% to about 0.1% of glycerin can be added to the solution.

DETAILED DESCRIPTION OF THE INVENTION

Trace amounts of peroxy compounds stabilized with a hydrogen peroxide stabilizer, especially diethylene triamine penta(methylene phosphonic acid) or 1-hydroxyethylidene-1,1-diphosphonic acid may be utilized as a preservative for drugs, eyewashes, or other solutions containing an active ingredient designed to be used in the ocular environment. The preservative according to the present invention may be used in the ocular environment. The preservative according to the present invention may be used in any ophthalmic solution as long as the active ingredient in that solution is compatible with trace amounts of the peroxy compounds. Also, virtually any peroxy compound may be used so long as it is hydrolyzed in water to produce hydrogen peroxide. Examples of such sources of hydrogen peroxide, which provide an effective resultant amount of hydrogen peroxide, include sodium perborate decahydrate, sodium peroxide and urea peroxide. It has been found that peracetic acid, an organic peroxy compound, cannot be stabilized utilizing the present system.

The full scope of the present invention includes ophthalmic active agent containing solutions as well as solutions which are ophthalmic active agent free. The former group contains at least one medicinal agent for application directly to the eye. The latter group comprises such solutions as preserved saline, preserved contact lens cleaning solutions, preserved contact lens stabilizing solutions, preserved wetting solutions, and preserved lubricating solutions, among others.

It is believed that most compounds, when preserved by the present invention, are compatible with trace amounts of hydrogen peroxide. The following is a non-exhaustive, non-limiting, illustrative list of active ingredients and excipients that are compatible with the preservative according to the present invention: atropine, homatropine, cyclopentolate, tropicamide, lachesine, dibutoline, oxyphenonium, eucatropine, ephedrine, carbachol, methacholine, pilocarpine hydrochloride, isoflurophate, physostigmine, neostigmine, lignocaine, cocaine, acetylcholine chloride, antazoline phosphate, betaxolol hydrochloride, demecarium bromide, dipivefrin hydrochloride, erythromycin, gentamicin sulfate, homatropine hydrobromide, idoxuridine, isosorbide, lanolin, naphazoline hydrochloride, neomycin sulfate, pheniramine maleate, polysorbate gelatin (Tween), pyrilamine maleate, scopolamine hydrobromide, hyaluronic acid, sodium hyaluronate, tetracaine hydrochloride, oxmetazolin, tetrahydrozoline hydrochloride, diclofenac sodium, dextran, carteolol, sulfanilamide, procaine, proparacaine hydrochloride, sulfisoxazole disolamine, indomethacin, clonidine, corynanthine, arachidonic acid, linoleic acid, H-thymidine and 3H-thymidine, inositol triphosphate, inositol phosphates, phosphatidylinositol and phosphatidylinositol phosphates.

Excipients of various types compatible with the present invention include, but are not limited to:

Polysorbate gelatin (Tween)
Dextran
Linolin
Inositol phosphates
Alkylsulfosuccinates
Sulfosuccinamate
Alkyl Silicone Sulfosuccinates
Alkylpolyether carboxylates
Alkylaryl polyethoxylamines
Alkylarylsulfonates
Alpha Olefin sulfonates
Alkyl surfates
Alkyl ether sulfates
Alkanol amides and alkamides
Alkylamphoterics
Amphoterics based on Alkyl imidazoline
Betaines
Alkylaminopropionates
Alkyliminodipropionates
Alkylamphoglycinates
Alkylamphocarboxyglycinates
Alkylamphocarboxypropinates
Alkylamphopropionates
Alkylamidopropylhydroxysultaines
Alkyletherhydroxypropylsultaines
Alkylamphopropylsulfonates
Quaternary ammonium polymers
Quaternary ammonium halides
Polyacrylamide
Polyacrylates
Polyvinyl pyrrolidone
Polyvinyl alcohol
Alkylalcohol ethoxylates
Hydroxyalkylcelluloses Alkylamidopropyl PG-Dimonium chloride phosphates
Alkylampho PG-glycinate phosphates
Glyceryl monoalkylates
Sorbitan alkylates (span)
Pluronics
Tetronics
Sodium alkyl sulfates
Sodium Butoxyethoxy Acetate
Phosphate esters
Glycosides
Polyglycosides
Mannitol
Sorbitol
Polyoxyethylene alkyl ethers
Grillosan having the formula

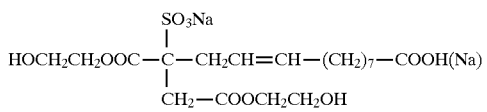

Guar gum
Sodium hyaluronate
Polyoxyl 40 stearate
Polyoxyolkylene dimethylpolysiloxane However, compounds having non-hindered hydroxyl groups attached to an aromatic ring, such as ketones and alcohols, or having a mercapto group, thioether, acetamido group, or aldehyde group will typically not be compatible. Such compounds believed not compatible with trace stabilized hydrogen peroxide include: noradrenaline, adrenaline, phenylephrine hydrochloride, amethocaine, oxybuprocaine, proxymethacaine, cromolyn sodium, benoxinate hydrochloride, chloramphenicol, chlortetracycline hydrochloride, dexamethasone, dichlorphenamide, echotiophate iodide, epinephrine bitartrate, fluorometholone, gramicidin, hydrocortisone, methazolamide, natamycin, prednisolone acetate, sulfacetamide ($N^1$-acetylsulfanilamide), tetracycline hydrochloride and timolol maleate.

The peroxy stabilizer used in the present invention may be any of the known stabilizers of peroxy compounds including phosphonates, phosphates, stannates, etc. However, physiologically compatible salts of phosphonic acids are preferred. Within this preferred group are (a) compounds of the formula

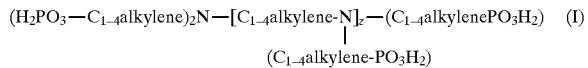

wherein z is an integer of from 0–3;
and (b) compounds of the formula

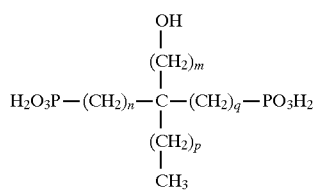

wherein each of n, m, p and q is independently 0–4, or physiologically compatible salts thereof. Highly preferred within formula I are compounds wherein z is 2 and compounds wherein each $C_{1-4}$ alkylene group is $C_1$ or $C_2$. Most preferred within formula I is diethylene triamine penta (methylene-phosphonic acid and the physiologically compatible salts thereof, marketed by Monsanto under the name Dequest® 2060. Highly preferred within formula II are compounds wherein n, m, p and q are each 0 or 1, most preferably zero, or a physiologically compatible salt thereof, marketed by Monsanto under the name Dequest® 2010.

Physiologically compatible salts of the compounds of formulae I and II include, for example, water soluble salts with conventional pharmaceutically acceptable cationic moieties, including the alkali metal, e.g. sodium, potassium, alkaline earth metal, e.g. calcium, ammonium and amine cations. Suitable amine salts include, for example, mono-, di-, and tri-lower alkyl amines, e.g. methylamine, ethylamine, diethylamine, triethylamine, dimethylamine, trimethylamine, propylamine, and the like; and mono-, di-, and tri-lower hydroxyalkyl amines, e.g. ethanolamine, diethanolamine, triethanolamine, glucamine, 2-hydroxypropylamine, and the like. By "lower" in the context of an alkyl group is meant an alkyl group having up to 6 carbon atoms, preferably up to 4 carbon atoms.

If desired, additional conventional stabilizers may be employed in conjunction with those of formulae I or II or combinations thereof in accordance with the present invention. Suitable conventional stabilizers include: water soluble stannates, such as an alkali metal or ammonium stannate, for example sodium stannate, alone or in combination with a water soluble phosphate, polyphosphate or etaphosphate salt, such as an alkali metal or ammonium salt thereof; or an amino polycarboxylic acid chelating agent, such as ethylene diamine tetraacetic acid, nitrilo triacetic acid or a water soluble salt thereof, such as an alkali metal or ammonium salt, especially the sodium salt, or mixtures thereof.

Still further peroxy stabilizers which may be used in the invention include a peroxide stabilizer selected from glycerin, polyvinyl alcohol having a molecular weight in the range of about 5,000 to about 150,000 (as long as water soluble) and being at least 80% hydrolized, propylene glycol, polyacrylic acid having a molecular weight of about 2,000 to about 100,000, diethylene glycol, and sodium hexamethaphosphate sodium polyphosphate (available from FMC under the name Hexaphos®).

The above stabilizers can be used in almost all indications previously mentioned to which the invention is applicable. However, when the solution is to come in contact with a hydrogel soft contact lens, stannate stabilizers are to be avoided as they tend to "cloud" the lens material.

Preferably, the concentration of the stabilizer of formula I or salt thereof is present in the stabilized composition in an amount between about 0.006 and about 0.02% by weight of the composition, and most preferably between about 0.006 and about 0.0120% by weight of the composition.

The stabilizer of formula II is present per 100 g of solution in an amount of at least about 0.024mmole (50 ppm), preferably 0.039 mmole (80 ppm) up to about 0.34 m mole (700 ppm) more preferably 0.049 mmole (100 ppm) up to about 0.29 mmole (600 ppm), most preferably 0.073 mmole (150 ppm) to about 0.19 mmole (400 ppm). The amounts in parentheses are for Dequest® 2010 which has a molecular weight of 206. Other stabilizers of formula II should be present in molar equivalents thereto.

The stabilizers other than those of formula I and II are employed in a physiologically tolerable amount, e.g. about 20 ppm to about 1000 ppm, preferably in an amount of at least 0.054 mmole (50 ppm), more preferably 0.087 mmole (80 ppm) to about 1.09 mmole (1000 ppm), still more preferably from about 0.109 mmole (100 ppm) to about 0.87 m mole (800 ppm), most preferably about 0.22 mmole (200 ppm) to about 0.65 mmole.

The pH of the stabilized solution is between about 5.5 and about 8. Preferably, the pH of the stabilized hydrogen peroxide solution is between about 6.0 and 8.0, most preferable between about 6.5 and 7.5. The pH can be adjusted as desired by incorporation of suitable amounts of acid or base of a physiologically tolerable nature in the amounts employed, e.g. hydrochloric acid and sodium hydroxide.

The pH of the stabilized solution presents another advantage over the prior art since the pH's of most existing ophthalmic solutions containing hydrogen peroxide are relatively low. The pH values of available hydrogen peroxide products for contact lenses are listed as follows:

| Name of the Product | pH | % of $H_2O_2$ |
|---|---|---|
| AOSept (CIBA Vision) | 6.3–6.6 | 3.3–3.5 |
| Lensept (CIBA Vision) | 3.98 | 3.4 |
| Oxysept (Allergan) | 3.28 | 3.3 |
| Mirasept (Coopervision) | 3.96 | 3.6 |
| Quiksept (Bausch & Lomb) | 3.57 | 3.5 |
| Puresept (Abbott Labs) | 3.83 | 3.4 |
| Softmate II (Barnes Hind) | 3.5–3.6 | 3.5 |

Also, there may be present in the stabilized hydrogen peroxide solution according to the present invention one or more conventional, substantially inert, physiologically acceptable tonicity enhancing agents. Suitable such agents include, for example, alkali metal halides, phosphates, hydrogen phosphate, and borates. Preferred are sodium chloride, sodium phosphate monobasic and sodium phosphate dibasic. The function of such tonicity enhancing agents is to assure approximate physiologic tonicity to the solution which is instilled in the eye or to help assure such tonicity upon dilution if dilution is necessary prior to contact with the eye due to peroxide content as indicated above.

Preferably sufficient tonicity enhancing agents are present in the solution so that it is substantially isotonic or, such that, upon decomposition or dilution of the hydrogen peroxide therein, the resulting solution is substantially isotonic, e.g. subtantially equivalent in tonicity to a 0.9% by weight aqueous sodium chloride solution.

A further optional ingredient is a thickener or viscosity enhancing agent. Any of the substances known in these categories which are ocularly acceptable can be used. Typical suitable thickeners include, inter alia, polyvinylalcohol, hydroxy ethylcellulose, etc. Thickeners may be present in any amount up to an amount sufficient to raise the overall solution viscosity to about 1000 cps, preferably to not more than 100 cps.

In general, the stabilized hydrogen peroxide solutions of the present invention are characterized by their extraordinary stability, even under accelerated conditions, for example by heating the solutions to 100° C. for 24 hours. Thus, the shelf life of these compositions is enhanced. Moreover, the instant compositions are characterized by either physiological tolerability subsequent to hydrogen peroxide decomposition.

Another advantage in using hydrogen peroxide in ophthalmic solutions is that the trace amount of hydrogen peroxide, especially less than 100 ppm, is destroyed once it comes in contact with the eye. For example, catalase existing in the eye tissue will cause the breakdown of the hydrogen peroxide into water and oxygen. As a result, the solution, upon application, becomes preservative free and greatly minimizes adverse reactions. The problems associated with other preservatives, such as the inability to break down innocuous compounds, are eliminated.

Formulation of the solutions of the invention can be made in any conventional manner. For example, all of the components other than the hydrogen peroxide and water can be placed in a container and fresh, preferably concentrated, hydrogen peroxide added thereto with mixing. Alternatively the dry components can be rubbed up with a small portion of liquid stabilizer, then the remainder of the stabilizer added, followed by the hydrogen peroxide, and most of the water. The viscosity enhancing agent, i.e. thickener, can then be added or the formed solution can be added to the thickener. One of ordinary skill in the art will be aware of numerous variations in the manner of formulating the solutions of the invention.

When it is desirable to "neutralize" the peroxide activity, any means known, such as rinsing, contacting the solution with platinum, catalase, or any other substance known to decompose hydrogen peroxide, will suffice. Additional physiological compatible peroxide neutralizing agents include reducing agent such as pyruvic acid and suitable salts thereof such as the sodium salt.

The following examples are presented for illustrative purposes and are not intended to limit the scope of this invention, but to demonstrate the stability of the peroxy solutions as stabilized in accordance with the present invention. All parts are by weight unless otherwise indicated.

EXAMPLE 1

Dissolve 0.610 g of sodium chloride, 0.005 g of sodium tetraborate.10 $H_2O$, 0.5 g of boric acid, 0.006 g of diethylene triamine penta(methylene phosphonic acid) and 0.1 g of tetrahydrozoline hydrochloride in 80 ml of purified deionized water. Add 0.0225 g of sodium perborate, add water up to 100 ml and adjust the pH to 7 by the addition dropwise of dilute hydrochloric acid or sodium hydroxide. The resulting solution is then heated to 100° C. for a period of 24 hours. The solution possesses a "hot stability" of above 90%, which is the ratio of the hydrogen peroxide present in the after-heated sample to the before-heated sample, multiplied by 100[%].

EXAMPLE 2

The procedure of example 1 is duplicated, except that 0.1 g of sodium [o-[(2,6-dichlorophenyl)amino]phenyl]acetate replace the tetrahydrozoline hydrochloride. The hot stability is found to be 91.0%.

EXAMPLE 3

The procedure of example 1 is duplicated, except that 0.5 g of pilocarpine hydrochloride replace the tetrahydrozoline hydrochloride. The hot stability is found to be 74.3%.

EXAMPLE 4

The procedure of example 1 is duplicated, except that 0.1 g of naphazoline hydrochloride replace the tetrahydrozoline hydrochloride. The hot stability is found to be 81.3%.

EXAMPLE 5

Dissolve 0.61 g of sodium chloride, 0.50 g boric acid, 0.005 g of sodium borate decahydrate, 0.05 g Grillosan (from RITA), and 0.006 g diethylene triamine penta (methylene phosphonic acid) in 80 ml of deionized water. Add 0.0238 g sodium perborate. Add water up to 100 ml and adjust the pH. to 7 by the addition dropwise of diluted hydrochloric acid or sodium hydroxide. The resulting solution is then heated to 100° C. for 24 hours. The hot stability of this solution i 93.1%.

EXAMPLE 6

The procedure of example 5 is duplicated except that the 0.05 g of Grillosan are replaced by 0.5 g propylene glycol. The hot stability of this solution is above 92%.

EXAMPLE 7

The procedure of example 5 is duplicated except that the 0.05 g of Grillosan are replaced by 0.5 g glycerin and an additional 0.01 g magnesium chloride. The hot stability of this solution is above 94%.

EXAMPLE 8

The procedure of example 5 is duplicated except that the 0.05 g of Grillosan are replaced by 0.1 g magnesium chloride. The hot stability of this solution is above 96%.

EXAMPLE 9

The procedure of example 5 is duplicated except that the 0.05 g of Grillosan are replaced by 0.5 g SIPEX EST-30 (sodium trideceth sulfate, CAS No. 68585-34-2, from Alcolac). The hot stability of this solution is above 92%.

EXAMPLE 10

The procedure of example 5 is duplicated except that the 0.05 g of Grillosan are replaced by 0.5 g Pluronic F-127 (BASF). The hot stability of this solution is above 93%.

EXAMPLE 11

Dissolve 0.35 g of sodium chloride, 0.35 g of potassium chloride, 0.58 g boric acid, 0.005 g sodium borate decahydrate and 0.006 g diethylene triamine penta(methylene phosphonic acid) in 80 ml of deionized water. Add 0.0238 g sodium perborate. Add water up to 100 ml and adjust the pH to 7 by the addition dropwise of diluted hydrochloric acid or sodium hydroxide. The hot stability of this solution is above 91%.

EXAMPLE 12

The procedure of example 11 is duplicated except that the 0.35 g of potassium chloride are replaced by 0.35 g of calcium chloride. The hot stability of this solution is above 93%.

EXAMPLE 13

The procedure of example 6 is duplicated except that the 0.5 g propylene glycol and 0.0238 g sodium perborate are replaced by 1 g propylene glycol and 0.0476 g sodium perborate. The hot stability of this solution is above 98%.

EXAMPLE 14

The procedure of example 13 is duplicated except that the 1 g propylene glycol is replaced by 0.1 g of citric acid. The hot stability of this solution is above 94%.

EXAMPLE 15

Dissolve 0.61 g of sodium chloride, 0.50 g boric acid, 0.005 g sodium borate decahydrate and 0.006 g diethylene triamine penta(methylene phosphonic acid) in 80 ml of deionized water. Add 0.0133 g sodium peroxide (from Mallinckrodt Cat. No. 7864). Add water up to 100 ml and adjust the pH to 7 by the additional dropwise of diluted hydrochloric acid or sodium hydroxide. The hot stability of this solution is above 93%.

EXAMPLE 16

The procedure of example 15 is duplicated except that the 0.0133 g sodium peroxide are replaced by 0.0138 g of urea hydrogen peroxide (from Aldrich Cat. No. 28913-2). The hot stability of this solution is above 53.6%.

EXAMPLE 17

Dissolve 0.61 g of sodium chloride, 0.50 g boric acid, 0.005 g sodium borate decahydrate, 0.1 g sulfanilamide (Sigma Cat. No. S-9251) and 0.006 g diethylene triamine penta(methylene phosphonic acid) in 80 ml of deionized water. Add 0.0238 g sodium perborate. Add water up to 100 ml and adjust the pH to 7 by the addition dropwise of diluted hydrochloric acid or sodium hydroxide. The hot stability of this solution is above 92%.

EXAMPLE 18

Dissolve 0.61 g of sodium chloride, 0.50 g boric acid, 0.005 g sodium borate decahydrate, and various amounts of 1-hydroxyethylidene-1,1-diphosphonic acid in 80 ml of deionized water. Add 0.0238 g sodium perborate. Add water up to 100 ml and adjust the pH to 7 by the addition dropwise of diluted hydrochloric acid or sodium hydroxide. The hot stabilities of those solutions are listed as follows:

| 1-Hydroxyethylidene-1,1-diphosphonic acid (g) | Hot Stability % |
|---|---|
| 0.03 | 87.1 |
| 0.05 | 90.3 |
| 0.08 | 96.8 |

EXAMPLE 19

This is an example of 1-hydroxyethylidene-1,1-diphosphonic acid as a stabilizer. The procedure of example 18 is duplicated except that various amounts of glycerin are added. The hot stabilities of these solutions are listed as follows:

| 1-Hydroxyethylidene-1,1-diphosphonic acid (g) | Glycerin (g) | Hot Stability % |
|---|---|---|
| 0.03 | 0.03 | 90.3 |
| 0.05 | 0.03 | 93.5 |
| 0.08 | 0.03 | 93.5 |
| 0.03 | 0.05 | 90.3 |
| 0.05 | 0.05 | 90.3 |
| 0.08 | 0.05 | 93.5 |

EXAMPLE 20

The procedure of example 17 is duplicated except that the 0.1 g sulfanilamide are replaced by 0.1 g hyaluronic acid (from Streptococcus Zooepidermicus). The hot stability of this solution is about 86%.

EXAMPLE 21

The procedure of example 20 is duplicated except that the 0.1 g hyaluronic acid (from Streptococcus Zooepidermicus) are replaced by 0.1 g hyaluronic acid (from Rooster Comb.). The hot stability of this solution is above 96%.

EXAMPLE 22

The procedure of example 20 is duplicated except that the 0.1 g hyaluronic acid are replaced by 0.1 g sodium hyaluronate. The hot stability of this solution is above 92%.

EXAMPLE 23

The procedure of example 22 is duplicated except that the 0.1 g sodium hyaluronate are replaced by 0.025 g oxymetazoline. The hot stability of this solution is above 87%.

EXAMPLE 24

Microbial preservative effectiveness test results of 50 ppm hydrogen peroxide in a borate buffer are listed as follows:

PRESERVATIVE EFFECTIVENESS TEST (50 ppm $H_2O_2$ solution)

| Challenge Microbe | Original Inoculum | Day 7 | Day 14 | Rechallenge on Day 14 with Inoculum |
|---|---|---|---|---|
| E. coli | $1.67 \times 10^6$ | Zero | Zero | $1.60 \times 10^5$ |
| P. aeruginosa | $2.04 \times 10^6$ | Zero | Zero | $1.94 \times 10^5$ |
| S. aereus | $1.09 \times 10^6$ | $1.75 \times 10^2$ | Zero | $1.74 \times 10^5$ |
| A. niger | $1.46 \times 10^5$ | $2.15 \times 10^4$ | $8.40 \times 10^3$ | $1.00 \times 10^5$ |
| C. albicans No. 1 | $1.63 \times 10^6$ | $8.00 \times 10^2$ | $2.40 \times 10^2$ | $1.41 \times 10^5$ |
| C. albicans No. 2 | $1.63 \times 10^6$ | $1.35 \times 10^3$ | $3.40 \times 10^2$ | $1.41 \times 10^5$ |
| C. albicans No. 3 | $1.63 \times 10^6$ | $1.75 \times 10^3$ | $4.90 \times 10^2$ | $1.41 \times 10^5$ |

| Challenge Microbe | Day 21 | Day 28 | % Reduction | Pass/Fail |
|---|---|---|---|---|
| E. coli | Zero | Zero | 100% | Pass |
| P. aeruginosa | Zero | Zero | 100% | Pass |
| S. aereus | Zero | Zero | 100% | Pass |
| A. niger | $4.65 \times 10^4$ | $4.50 \times 10^4$ | | Pass |
| C. albicans No. 1 | $1.09 \times 10^5$ | $3.90 \times 10^4$ | | Pass |
| C. albicans No. 2 | $1.12 \times 10^5$ | $3.55 \times 10^4$ | | Pass |
| C. albicans No. 3 | $1.26 \times 10^5$ | $3.40 \times 10^4$ | | Pass |

What is claimed is:

1. A contact lens treatment solution, comprising a source of hydrogen peroxide in concentration sufficient to act as a preservative for an ophthalmic solution, wherein said hydrogen peroxide concentration is less than an amount which is intolerable for direct application to the eye.

2. A contact lens treatment solution of claim 1, comprising a source of hydrogen peroxide resulting in 0.001 to 0.10 weight percent hydrogen peroxide.

3. A contact lens treatment solution of claim 1, comprising:
    (a) a source of hydrogen peroxide resulting in 0.001 to 0.10 weight percent hydrogen peroxide;
    (b) a tonicity-enhancing agent in an amount sufficient to form a substantially isotonic solution; and
    (c) water.

4. A contact lens treatment solution of claim 1, wherein said source of hydrogen peroxide is selected from the group consisting of hydrogen peroxide, sodium perborate decahydrate, sodium peroxide and urea peroxide.

5. A contact lens treatment solution of claim 2, wherein said source of hydrogen peroxide is selected from the group consisting of hydrogen peroxide, sodium perborate decahydrate, sodium peroxide and urea peroxide.

6. A method of treating a contact lens, comprising contacting the lens with a preserved composition including:
    (1) a source of hydrogen peroxide in an amount sufficient to generate about 0.001 to 0.10 weight percent hydrogen peroxide in solution as a preservative;
    (2) a tonicity adjusting agent; and
    (3) water.

7. The method of claim 6, wherein said resultant amount of hydrogen peroxide is from 0.001% to 0.10% by weight.

8. The method of claim 6, wherein said trace amount of hydrogen peroxide is the only preservative used.

9. The method of claim 6, wherein said hydrogen peroxide source is selected from the group consisting of hydrogen peroxide, sodium perborate decahydrate, sodium peroxide and urea peroxide.

10. The method of claim 6, and further comprising the step of adding a tonicity agent.

11. The method of claim 6 further comprising the step of adjusting the pH of said solution from 5.5 to 8.

12. The method according to claim 11, and further comprising the step of adding to said solution a buffer and saline in an amount so as to render the solution substantially isotonic.

13. The method of claim 12 wherein the solution has a tonicity of 0.9% sodium chloride.

14. A method of treating a contact lens as recited in claim 6, comprising:
    (a) contacting the lens with a composition effective in disinfecting or cleaning; and
    (b) rinsing the lens with a composition including:
        (1) a source of hydrogen peroxide in an amount sufficient to generate about 0.001 to 0.10 weight percent hydrogen peroxide in solution;
        (2) a toncity adjusting agent; and
        (3) water.

15. A method of storing a contact lens for an extended period in the absence of substantial microbial growth, comprising the steps of:
    (a) placing a lens in a container; and
    (b) placing an antimicrobial buffered saline solution in the container in an amount sufficient to immerse the lens, the antimicrobial buffered saline solution including:
        (1) a source of hydrogen peroxide in an amount sufficient to generate about 0.001 to 0.10 weight percent hydrogen peroxide in solution;
        (2) a tonicity adjusting agent; and
        (3) water.

16. A method of claim 15, comprising the steps of:
    (a) providing a contact lens substantially free of biological matter;
    (b) placing the lens in a container; and
    (c) placing an antimicrobial buffered saline solution in the container in an amount sufficient to immerse the lens, the antimicrobial buffered saline solution including:
        (1) a source of hydrogen peroxide in an amount sufficient to generate about 0.001 to 0.10 weight percent hydrogen peroxide in solution;
        (2) a tonicity adjusting agent; and
        (3) water.

* * * * *